United States Patent
DePinho et al.

(10) Patent No.: US 6,639,121 B1
(45) Date of Patent: Oct. 28, 2003

(54) INDUCIBLE CANCER MODEL TO STUDY THE MOLECULAR BASIS OF HOST TUMOR CELL INTERACTIONS IN VIVO

(75) Inventors: Ronald A. DePinho, Boston, MA (US); Lynda Chin, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 09/619,247

(22) Filed: Jul. 19, 2000

Related U.S. Application Data

(60) Provisional application No. 60/146,197, filed on Jul. 29, 1999.

(51) Int. Cl.$^7$ ............... A01K 67/033; A01K 67/00; G01N 33/00; C12N 15/00; C12N 5/00
(52) U.S. Cl. .................. 800/10; 800/3; 800/8; 800/9; 800/18; 435/455; 435/325; 435/320.1
(58) Field of Search ............... 435/455, 463, 435/320.1, 325; 800/18, 21, 22, 25, 3

(56) References Cited

U.S. PATENT DOCUMENTS

| | | | |
|---|---|---|---|
| 4,736,866 A | 4/1988 | Leder et al. | 800/10 |
| 5,175,383 A | 12/1992 | Leder et al. | 800/10 |
| 5,859,310 A | 1/1999 | Bujard et al. | 800/2 |
| 5,919,997 A | * 7/1999 | Beach et al. | 800/18 |

FOREIGN PATENT DOCUMENTS

| | | |
|---|---|---|
| WO | WO 91/15111 | 10/1991 |
| WO | WO 99/32619 | 7/1999 |

OTHER PUBLICATIONS

Chang, M–Y, et al. A Ribozyme Specifically Suppresses Transformation and Tumorigenicity of Ha–ras–oncogene–transformed NIH/3T3 cell lines. J. Cancer. Res. Clin. Onco. 123:91–99, 1997.*
WALL; Transgenic Livestock : Progress and Prospects for the Future, 1996, Theriogenology45: 57–68.*
Houdebine; Production of pharmaceutical proteins from transgenic animals, 1994, Journal of Biotechnology 34: 269–287.*
Hammer et. al.; Genetic Engineering of Mammalian Embryos, 1986, J. Anim. Sci. 63: 269–278.*
Ebert et. al.; A Moloney MLV–Rat Somatotropin Fusion Gene Produces Biologically Active Somatotropin in a Transgenic Pig, 1988.*
Mullins et. al.; Perspective Series: Molecular Medicine in Genetically Engineered Animals, 1996, J. Clin> INvest. vol. 97, No. 7: 1557–1560.*
Kappel et. al.; Regulating gene expression in transgenic animals, 1992, Current Biology, 548–553.*
Strojek et. al.; The Use of Transgenic Animal Techniques for Livestock Improvement, 1988, Genetic Engineeruing: Principles and methods, vol. 10: 221–246.*
Moreadth et. al.; Gene targeting in embryonic stem cells: the new physiology and metabolism, 1997, J. Mol. Med. 75: 208–216.*
Chin et. al.; Cooperative effects of INK4a and ras in melanoma susceptibility in vivo, 1997, Genes & Development:2822–2834.*
Kistner et. al.; Doxyccline–mediated quantitative and tissue–speciic control of gene expression in transgenic mice, 1996, Proc. Natl. Acad.Sci., vol. 93:10933–10938.*
Adams et al., "The c–myc oncogene driven by immunoglobulin enhancers induces lymphoid malignancy in transgenic mice," *Nature*, 1985, 318:533–538.
Adams et al., "The Transgenic Window on Lymphoid Malignancy," *Genetic Basis for Carcinogenesis—Tumor Suppressor Genes and Oncogenes*, Proceedings of the 20$^{th}$ International Symposium of The Princess Takamatsu Cancer Research Fund, Tokyo, 1989, pp. 297–309.
Atkins and Gershell, "Selective anticancer drugs," *Nature*, 2002, 1:491–492.
Carson and Lois, "Cancer progression and p53," *Lancet*, 1995, 346:1009–1011.
Castrodale, "Leading Genomic Approaches for Breaking Bottlenecks in Drug Discovery and Development," CHI Reports.
Courtneidge and Plowman, "The discovery and validation of new drug targets in cancer," *Curr. Opin. Biotechnol.*, 1998, 9:632–636.
de Vries et al., "Increased susceptibility to ultraviolet–B and carcinogens of mice lacking the DNA excision repair gene XPA," *Nature*, 1995, 377:169–173.
Donehower et al., "Mice deficient for p53 are developmentally normal but susceptible to spontaneous tumours," *Nature*, 1992, 356:215–221.
Efrat et al., "Conditional transformation of a pancreatic α–cell line derived from transgenic mice expressing a tetracycline–regulated oncogene," *Proc. Natl. Acad. Sci. USA*, 1995, 92:3576–3580.
Ewald et al., "Time–Sensitive Reversal of Hyperplasia in Transgenic Mice Expressing SV40 T Antigen," *Science*, 1996, 273:1384–1386.
Fearon and Vogelstein, "A Genetic Model for Colorectal Tumorigenesis," *Cell*, 1990, 61:759–767.
Fearon and Vogelstein, "Tumor Suppressor and DNA Repair Gene Defects in Human Cancer," *Cancer Medicine*, 4$^{th}$ Edition, Holland et al. (eds.), 1997, Williams & Wilkins, Chapter 6, pp. 97–117.

(List continued on next page.)

*Primary Examiner*—Deborah Crouch
*Assistant Examiner*—Thaian N. Ton
(74) *Attorney, Agent, or Firm*—Fish & Richardson P.C.

(57) ABSTRACT

A non-human mammal having incorporated into its genome an expression construct in which nucleic acid encoding an oncogene is operably linked to an inducible promoter; the mammal further has a genetic mutation that causes it to have an increased susceptibility to cancer.

47 Claims, 6 Drawing Sheets

OTHER PUBLICATIONS

Felsher et al., "Reversible Tumorigenesis by MYC in Hematopoietic Lineages," *Molecular Cell*, 1999, 4:199–207.

Fero et al., "A Syndrome of Multiorgan Hyperplasia with Features of Gigantism, Tumorigenesis, and Female Sterility in p27$^{Kip1}$–Deficient Mice," *Cell*, 1996, 85:733–744.

Hanahan and Weinberg, "The Hallmarks of Cancer," *Cell*, 2000, 100:57–70.

Harrison et al., "Microsomal epoxide hydrolase gene polymorphism and susceptibility to colon cancer," *Br. J. Cancer*, 1999, 79(1):168–171.

Herlyn and Satyamoorthy, "Molecular Biology of Cutaneous Melanoma," *Principles and Practice of Oncology*, 6$^{th}$ Edition, de Vita et al. (eds.), pp. 2003–2012.

Honda et al., "Expression of p210$^{bcr/abl}$ by Metallothionein Promoter Induced T–Cell Leukemia in Transgenic Mice," *Blood*, 1995, 85(10):2853–2861.

Hooper, "Tumour suppressor gene mutations in humans and mice: parallels and contrasts," *EMBO J.*, 1998, 17(23):6783–6789.

Huettner et al., "Reversibility of acute B–cell leukaemia induced by BCR–ABL1," *Nature Genetics*, 2000, 24:57–60.

Jonkers and Berns, "Conditional Mouse Models of Sporadic Cancer," *Nature*, 2002, 2:251–265.

Kamijo et al., "Tumor Suppression at the Mouse INK4α Locus Mediated by the Alternative Reading Frame Product p19$^{ARF}$," *Cell*, 1997, 91:649–659.

Kinzler and Vogelstein, "Gatekeepers and caretakers," *Nature*, 1997, 386:761, 763.

Kuhlmann, "Alternative strategies in drug development: clinical pharmacological aspects," *Int. J. Clin. Pharmacol. Ther.*, 1999, 37(12):575–583.

Kumar and Farr–Jones, "The hunt for utility," Post–Map Workplan Report, Published on Feb. 20, 2001, 20 pgs.

Kumar, "Industrializing tox," Technology Focus Report, Published on Aug. 6, 2001, 7 pgs.

Kumar, "Marking the future," Managing Complexity Report, Published on Apr. 22, 2002, 8 pgs.

Matsui et al., "Development of Mammary Hyperplasia and Neoplasia in MMTV–TGFα Transgenic Mice," *Cell*, 1990, 61:1147–1155.

Muller et al., "Single–Step Induction of Mammary Adenocarcinoma in Transgenic Mice Bearing th Activated c–neu Oncogene," *Cell*, 1988, 54:105–115.

Nuttall, "Drug Discovery and Target Validation," *Cells Tissues Organs*, 2001, 169:265–271.

Pelengaris et al., "Reversible Activation of c–Myc in Skin: Induction of a Complex Neoplastic Phenotype by a Single Oncogenic Lesion," *Molecular Cell*, 1999, 3:565–577.

Petricoin et al., "Clinical Proteomics: Translating Benchside Promise into Bedside Reality," *Nature*, 2002, 1:683–695.

Prolla et al., "Tumour susceptibility and spontaneous mutation in mice deficient in Mlh1, Pms1 and Pms2 DNA mismatch repair," *Nature Genetics*, 1998, 18:276–279.

Reddy and Kaelin Jr., "Using cancer genetics to guide the selection of anticancer drug targets," *Curr. Opin. Pharmacol.*, 2002, 2:366–373.

Reitmair et al., "Spontaneous Intestinal Carcinomas and Skin Neoplasms in Msh2–deficient Mice," *Cancer Res.*, 1996, 56:3842–3849.

Schatzkin and Gail, "The Promise and Peril of Surrogate End Points in Cancer Research," *Nature*, 2002, 2:1–9.

Schichman and Croce, "Oncogenes," *Cancer Medicine*, 4$^{th}$ Edition, Holland et al. (eds.), 1997, Williams & Wilkin, Chapter 5, pp. 85–95.

Schreiber–Agus et al., "Role of Mxi1 in ageing organ systems and the regulation of normal and neoplastic growth," *Nature*, 1998, 393:483–487.

Serrano et al., "Role of the INK4α Locus in Tumor Suppression and Cell Mortality," *Cell*, 1996, 85:27–37.

Sidransky, "Emerging Molecular Markers of Cancer," *Nature*, 2002, 2:210–219.

Stambolic et al., "Negative Regulation of PKB/Akt–Dependent Cell Survival by the Tumor Suppressor PTEN," *Cell*, 1998, 95:29–39.

Stevanovic, "Identification of Tumour–Associated T–Cell Epitopes for Vaccine Development," *Nature*, 2002, 2:1–7.

Taketo, "Apc Gene Knockout Mice as a Model for Familial Adenomatous Polyposis," *Progress in Experimental Tumor Research*, Bertino (ed.), Karger, Basil, 1999, vol. 35, pp. 109–119.

Tam et al., "Tetracycline–regulatable expression of RAS in mouse melnocytes and melanomas," *Proceedings—Cancer Biology and the Mutant Mouse: New Methods, New Models, New Insights*, Celebrating the 10$^{th}$ Anniversary of the AACR Special Conferences in Cancer Research, Jan. 31–Feb. 5, 1999, Keystone Resortland Conference Center, Keystone, Colorado, p. B–7.

Taylor et al., "Real–time molecular and cellular analysis: the new frontier of drug discovery," *Curr. Opin. Biotechnol*, 2001, 12:75–81.

Tolcher, "Novel Compounds in the Therapy of Breast Cancer: Opportunities for Integration with Docetaxel," *The Oncologist*, 2001, 6(Suppl. 3):40–44.

Usdin, "Understanding accelerated approval," Regulation Report, Published on Sep. 17, 2001, 3 pgs.

Wang et al., "Mammary hyperplasia and carcinoma in MMTV–cyclin D1 transgenic mice," *Nature*, 1994, 369:669–671.

Weissenberger et al., "Development and malignant progression of astrocytomas in GFAP–v–src transgenic mice," *Oncogene*, 1997, 14:2005–2013.

Weston and Harris, "Chemical Carcinogenesis," *Cancer Medicine*, 4$^{th}$ Edition, Holland et al. (eds.), 1997, Williams & Wilkins, Chapter 13, pp. 261–276.

Wiley, "Genomics in the Real World," *Current Pharmaceutical Design*, 1998, 4:417–422.

Williams et al., "Extensie contribution of Rb–deficient cells to adult chimeric mice with limited histopathological consequences," *EMBO J.*, 1994, 13(18):4251–4259.

Workman, "Scoring a bull's–eye against cancer genome targets," *Curr. Opin. Pharmacol.*, 2001, 1:342–352.

Xie et al., "Conditional expression of the ErbB2 oncogene elicits reversible hyperplasia in stratified epithelia and up–regulation of TGFα expression in transgenic mice," *Oncogene*, 1999, 18:3593–3607.

Chin et al., Familial Melanoma Gene, INK4a, Cooperates with Activated RAS in Development of Melanoma: A Mouse Model. Journal of Investigative Dermatology 110(4):498 (1998), Abstract No. 154.

Barber et al., "Potassium Conductances and Proliferation in Conditionally Immortalized Renal Glomerular Mesangial Cells from the H–2K$^b$–tsA58 Transgenic Mouse," Biochimica et Biophysica Acta 1355:191–203 (1997).

Chin et al., "Flipping the Oncogene Switch: Illumination of Tumor Maintenance and Regression," Trends in Genetics 16:147–150 (2000).

Jones et al., "Analysis of Tumor Suppressor Genes Using Transgenic Mice," Methods: A Companion to Methods in Enzymology 8:247–258 (1995).

Loidi et al., "Complex Regulation of Prothymosin Alpha in Mammary Tumors Arising in Transgenic Mice," Life Sciences 64:2125–2133 (1999).

Rudolph et al., "Genetically Modified Animals in Pharmacological Research: Future Trends," European Journal of Pharmacology 375:327–337 (1999).

Vile et al., "Tissue–Specific Gene Expression from Mo–MLV Retroviral Vectors with Hybrid LTRs Containing the Murine Tyrosinase Enhancer/Promoter," Virology 214:307–313 (1995).

* cited by examiner

INDUCIBLE CANCER MODEL TO STUDY THE MOLECULAR BASIS OF HOST TUMOR CELL INTERACTIONS IN VIVO

STATEMENT AS TO FEDERALLY SPONSORED RESEARCH

This invention was funded with grants received from the National Institutes of Health (Grant Nos. AR02104 and EY11267). Accordingly, the government has certain rights in this invention.

This application claims the benefit of Provisional application Ser. No. 60/146,197, filed Jul. 29, 1999.

BACKGROUND OF THE INVENTION

Advanced malignancy represents the phenotypic endpoint of successive genetic lesions that impact on the function and regulation of oncogenes and tumor suppressor genes[1]. The established tumor is maintained through complex and poorly understood host-tumor interactions guiding processes such as angiogenesis and immune sequestration. The numerous and diverse genetic alterations that accompany tumor-ogenesis raises questions as to whether experimental cancer-promoting mutations remain relevant to tumor maintenance.

SUMMARY OF INVENTION

Melanoma genesis and maintenance were shown to be strictly dependent upon H-RAS$^{V12G}$ expression in a novel doxycycline-inducible H-RAS$^{V12G}$ INK4a null mouse melanoma model. Withdrawal of doxycycline and H-RAS$^{V12G}$ down-regulation resulted in clinical and histological regression of primary and explanted tumors. The initial stages of regression were highlighted by dramatic activation of apoptosis in the tumor cell and host-derived endothelial cells. Although the regulation of VEGF was found to be RAS-dependent in vitro, the failure of persistent endogenous and enforced VEGF expression to sustain tumor viability indicated that the tumor maintenance actions of activated RAS extend beyond the regulation of VEGF gene expression in vivo. Together these data provide genetic evidence that H-RAS$^{V12G}$ plays a critical role in both the genesis and maintenance of solid tumors.

Accordingly, the invention features a non-human mammal having incorporated into its genome an expression construct including nucleic acid encoding an oncogene operably linked to an inducible promoter, the mammal further having a genetic mutation that causes it to have a greater susceptibility to cancer than a mammal not having that mutation.

In preferred embodiments: the mammal is a mouse; the oncogene is ras; the ras gene has an activating mutation; the inducible promoter can be induced by doxycycline; and the mutation is in DNA encoding a tumor suppressor such as INK4.

In a second, related aspect, the invention features a non-human mammal having incorporated into its genome: (i) a first expression construct in which a reverse tetracycline transactivator is operably linked to a tissue-specific promoter; and (ii) a second expression construct in which nucleic acid encoding an oncogene is operably linked to a promoter that can be regulated by the reverse tetracycline transactivator; the mammal further has a genetic mutation that causes it to have greater susceptibility to cancer than a mammal that does not have the mutation. In preferred embodiments of this aspect of the invention, the tissue-specific promoter is a tyrosine promoter, and expression of the oncogene results in the mammal having greater susceptibility to cancer than a mammal having the mutation but not expressing the oncogene.

In a third, related aspect, the invention features a non-human mammal having incorporated into its genome: (i) a first expression construct in which a reverse tetracycline transactivator is operably linked to a tyrosinase promoter; and (ii) a second expression construct in which nucleic acid encoding ras is operably linked to a promoter than can be regulated by the reverse tetracycline transactivator.

The invention can be used as a model for any cancer, and in particular solid tumors such as melanoma. The oncogene linked to the inducible promoter and/or the mutation in the genome of the mammal are chosen to direct development of the desired tumor type.

A. Photomicrograph of SCID mice maintained on (a) doxycycline and off (b) doxycycline after subcutaneous injection of R192 cells. Arrows: subcutaneous tumors. Similar experiments performed with multiple independently derived melanoma cell lines were summarized in the table. "Duration" refers to the period of observation in months.

B. Growth curve determinations of three independently derived melanoma cell lines with and without doxycycline supplementation in media (see Methods). Solid lines: doxycycline-treated; Dotted lines: doxycycline-free. Note cultures were subconfluent during the first 5 days.

Figure 4:
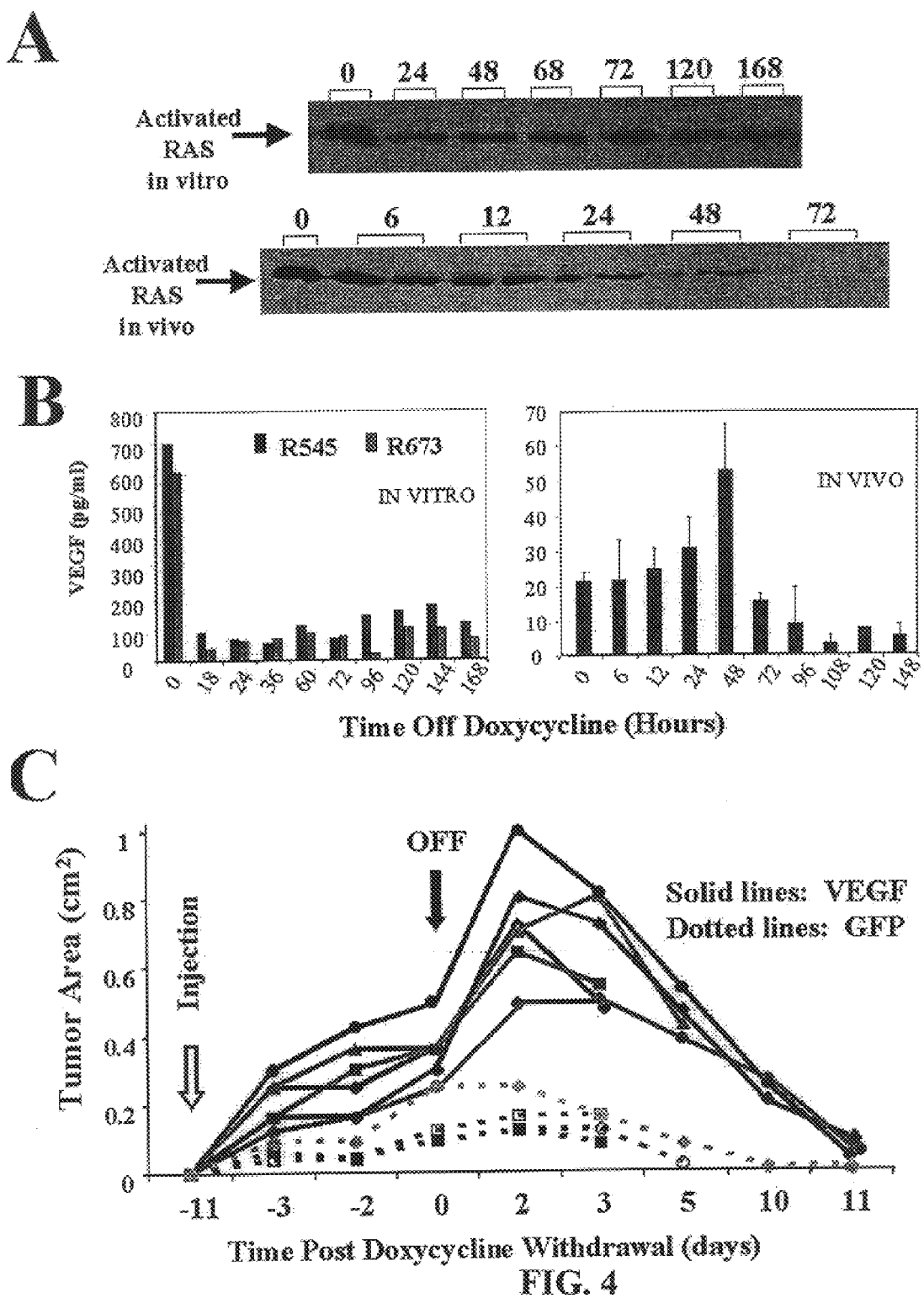
Figure 4:
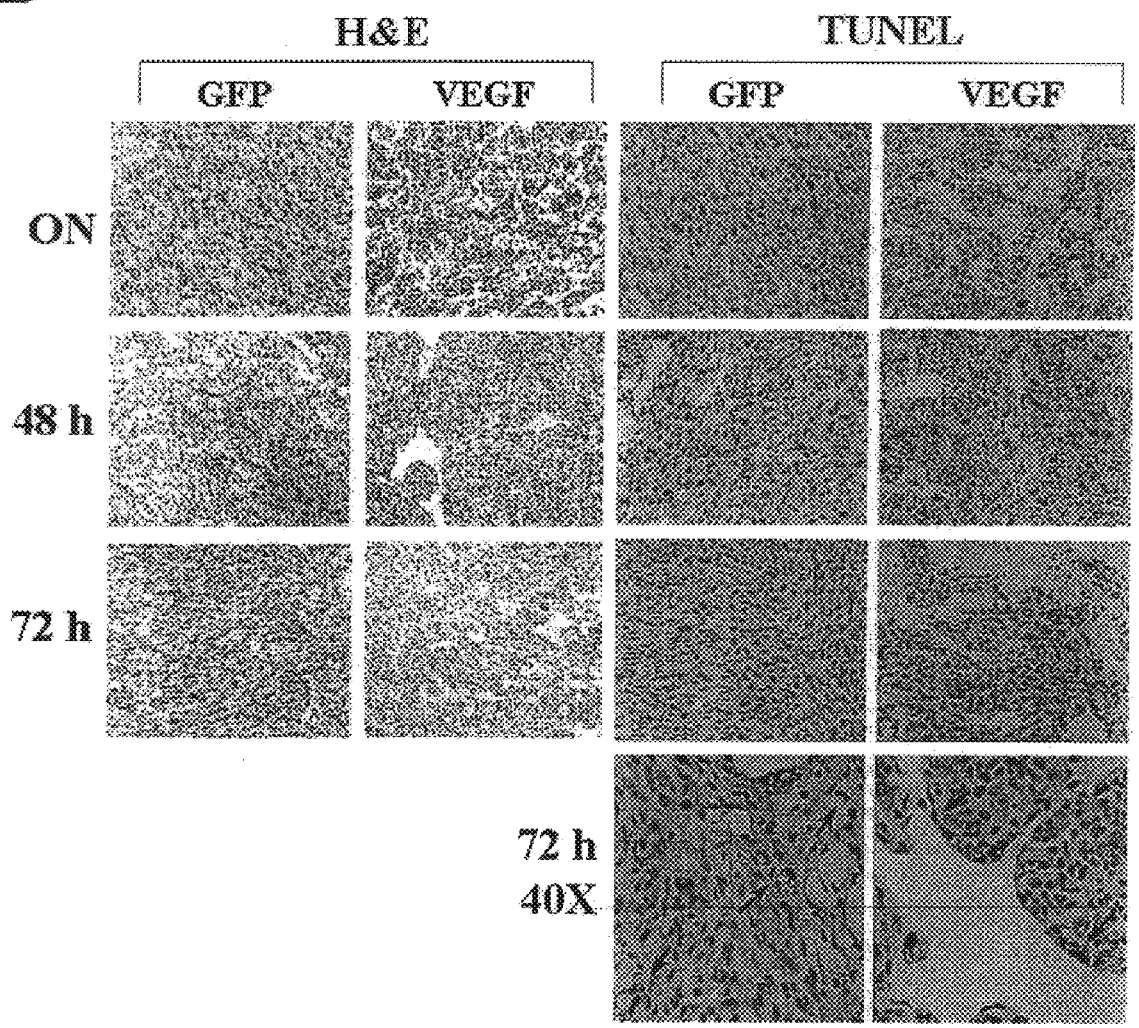

FIG. 4. VEGF is not sufficient to sustain tumor viability following doxycycline withdrawal.

A. RAS activity levels after withdrawal from doxycycline in vivo and in vitro. R545 melanoma cells in cultures or R545 derived SCID tumors were subjected to Raf-GST pull down assay (see Methods) to determine level of RAS activity at indicated time after doxycycline withdrawal. For in vivo assay, two independently derived samples were assayed except for the 0 hour time point.

B. Endogenous VEGF protein levels of cultured R545 and R673 cells (Left), as well as SCID derived R545 tumors (Right).

C. Enforced VEGF expression in R545 melanoma cells is not sufficient to block tumor regression in SCID mice after doxycycline withdrawal. Transduced cells were injected on day-11 and doxycycline was withdrawn from drinking water on day 0.

D. Photomicrographs of H&E and TUNEL stainings of SCID tumors from C. Note large ectactic vascular spaces in VEGF-transduced tumors. Increase in # of TUNEL positive nuclei (both tumor and endothelial cells) was evident in both 48 hours and 72 hours after doxycycline withdrawal in tumors with or without enforced VEGF expression. Arrows: TUNEL positive endothelial cells lining vascular spaces.

DETAILED DESCRIPTION OF THE INVENTION

Figure 1:
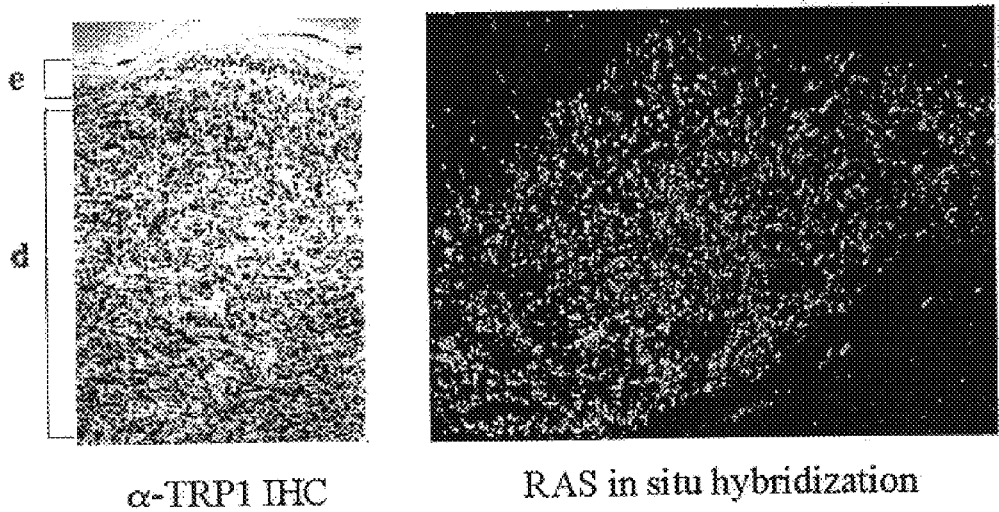
FIG. 1. Inducible Tyr/Tet-RAS transgenic mice on INK4a deficient background developed cutaneous melanomas.
  A. Summary of tumor incidence in the Tyr/Tet-RAS-INK4a null colony and impact of doxycycline treatment.
  B. Left: anti-TRP1 staining of a primary cutaneous melanoma. Note strong immunoreactivity in dermal nodule with overlying intact epidermis; e=epidermis; d=dermis. Right: in situ hybridization for H-RAS$^{V12G}$ transcript in a primary melanoma nodule.

To develop a cancer model in which dominantly acting oncoproteins are somatically regulated in vivo, transgenic mouse lines harboring the reverse tetracycline transactivator[2] under the control of the tyrosinase gene promoter-enhancer elements (designated Tyr-rtTA) and another containing the H-RAS$^{V12G}$ open reading frame driven by a minimal promoter containing multimerized tet-operons.[2,3] (designated Tet-RAS) were inter-crossed with INK4a+/− mice to generate cohorts of single and double transgenic mice (designated Tyr/Tet-RAS) homozygous null for INK4a. Upon weaning, a subset of single and double transgenic INK4a −/− mice were administered doxycycline in the drinking water[4]. In the doxycycline-treated group, 10 of 40 Tyr/Tet-RAS INK4a−/− mice developed melanomas with an average latency of 60 days (FIG. 1A). In contrast, the untreated Tyr/Tet-RAS INK4a−/− mice (n=12) or treated Tet-RAS INK4a−/− mice (n=23) failed to develop melanomas. The Tyr/Tet-RAS INK4a−/− melanomas shared all of the macroscopic features of the constitutive Tyr-RAS INK4a−/− melanomas[5], manifesting as amelanotic, invasive and highly vascular tumors—features reminiscent of nodular-type melanoma in humans (for example, see FIGS. 2A&B). Histological examination revealed a spindle morphology with anaplastic and pleiomorphic cytology (FIG. 2C), strong immunoreactivity to the early melanocyte-specific marker tyrosinase-related protein-1 (TRP-1)[6], and robust H-RAS$^{V12G}$ expression and activity in tumors and tumor-derived cell lines in culture (FIG. 1B and FIG. 4A).

Figure 2:
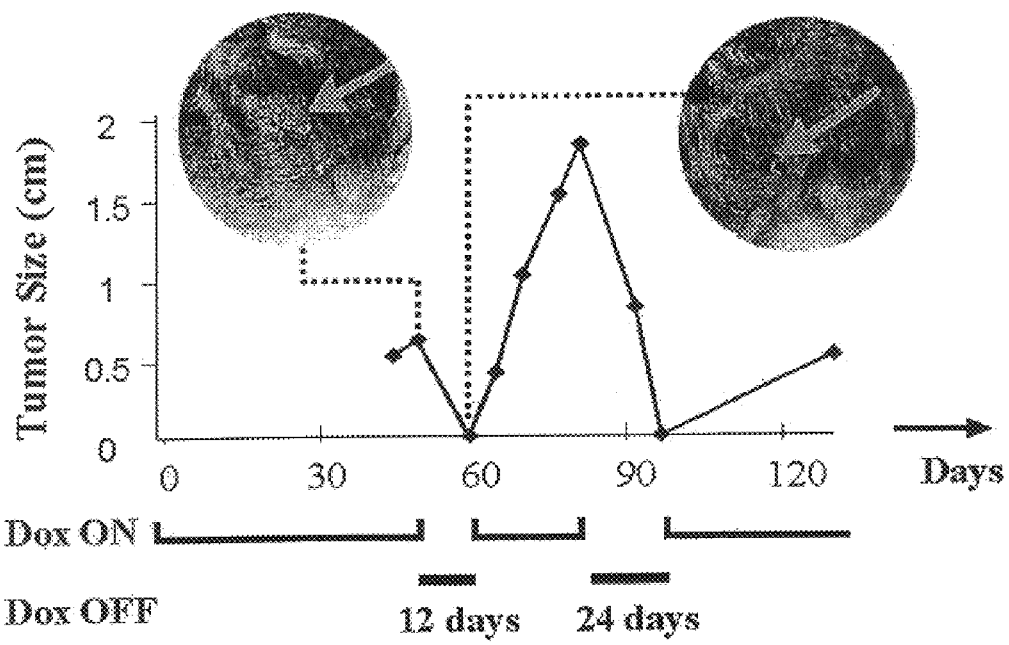
FIG. 2. Activated RAS expression is necessary to maintain growth of established cutaneous melanomas in vivo.
  A. Tumor from R348 (Tet-RAS founder line #65) was measured at intervals and longest dimension was plotted against time. Time 0 represents initial induction with doxycycline. Red brackets indicate periods during which the animal was ON doxycycline induction. Blue lines indicate period without doxycycline administration. Insets: Representative photographs of R348 tumor taken on respective time points (ON and 12 days OFF) during the first cycle of doxycycline treatment. All primary melanomas (n=10) exhibited a strong regression response following doxycycline withdrawal, although 2 of the largest tumors recurred at the site as slow growing tumors of indeterminate type (see text). Two fully regressed tumor-bearing mice were re-induced to form large tumors, one of which regressed fully upon doxycycline withdrawal (depicted here), while growth of the other tumor remained stable for additional 10 days before sacrifice.
  B. Regression of primary melanoma in R767. (a)=ON, (b)=3 days and (c)=10 days OFF.
  C. Photomicrographs of H&E sections of one of the tumors in R348 measured and depicted in A. Top panel 200x, lower panel 400xmagnification. ON=histology of the tumor biopsied while on doxycycline. Note anaplastic and pleiomorphic large cells. 48 Hr OFF= Histology of the tumor biopsied 48 hours after withdrawal of doxycycline. Note more orderly spindle morphology. 12 D OFF=histology of the site where tumor was biopsied 12 days after withdrawal of doxycycline. Note intact epidermis and scattered foci of transformed cells (arrows). * denotes hair follicle; e=epidermis.
  D. Photomicrographs of TUNEL (top panel) staining of tumors from mouse R405 (Tet-RAS founder line #72) biopsied ON (left) and 72 Hrs OFF doxycycline (middle). Higher power magnification (right) of the bracketed region in middle. Arrow=TUNEL positivity in endothelial cell. Middle panel shows Ki67 immunostaining for detection of S phase nuclei. Bottom panel depicts anti-CD34 staining patterns of the same tissues.
Figure 2:
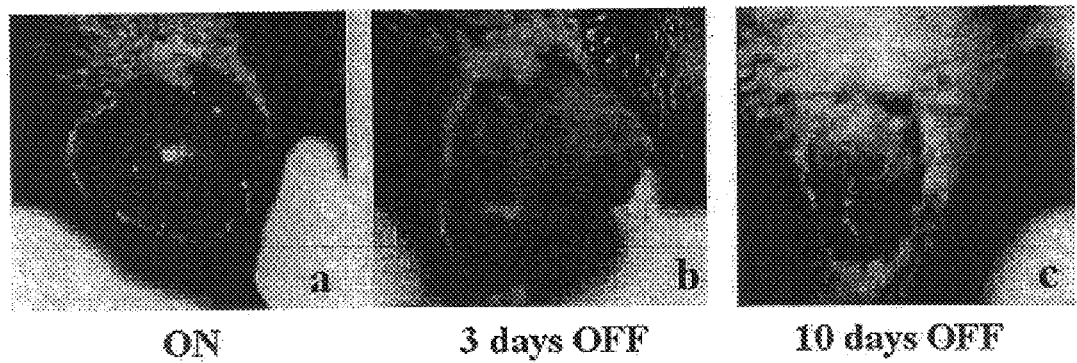
Figure 2:
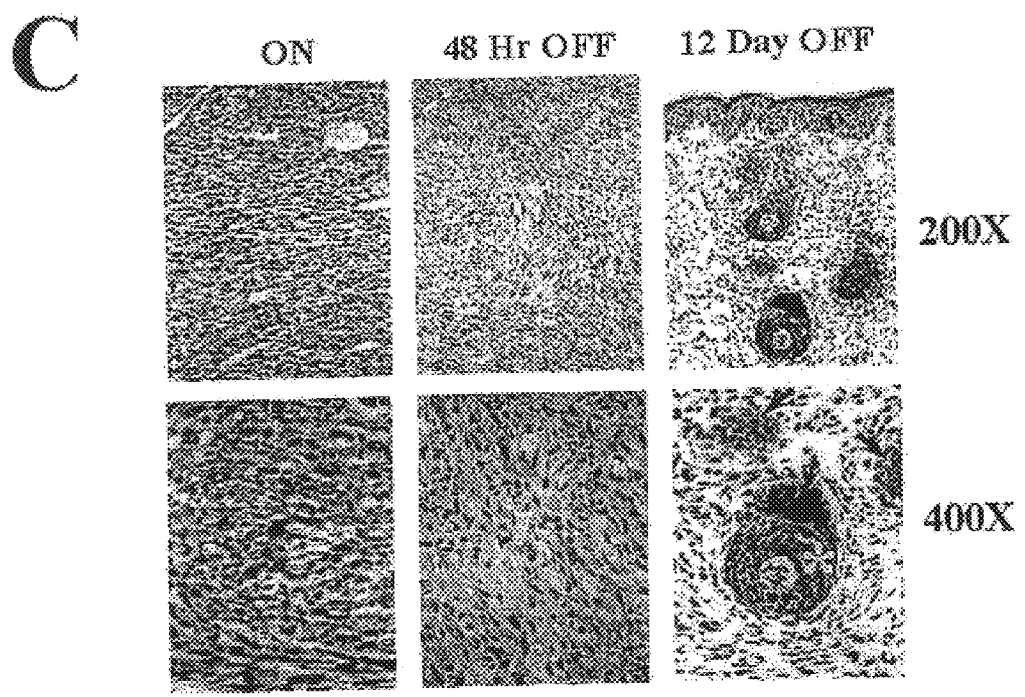
Figure 2:
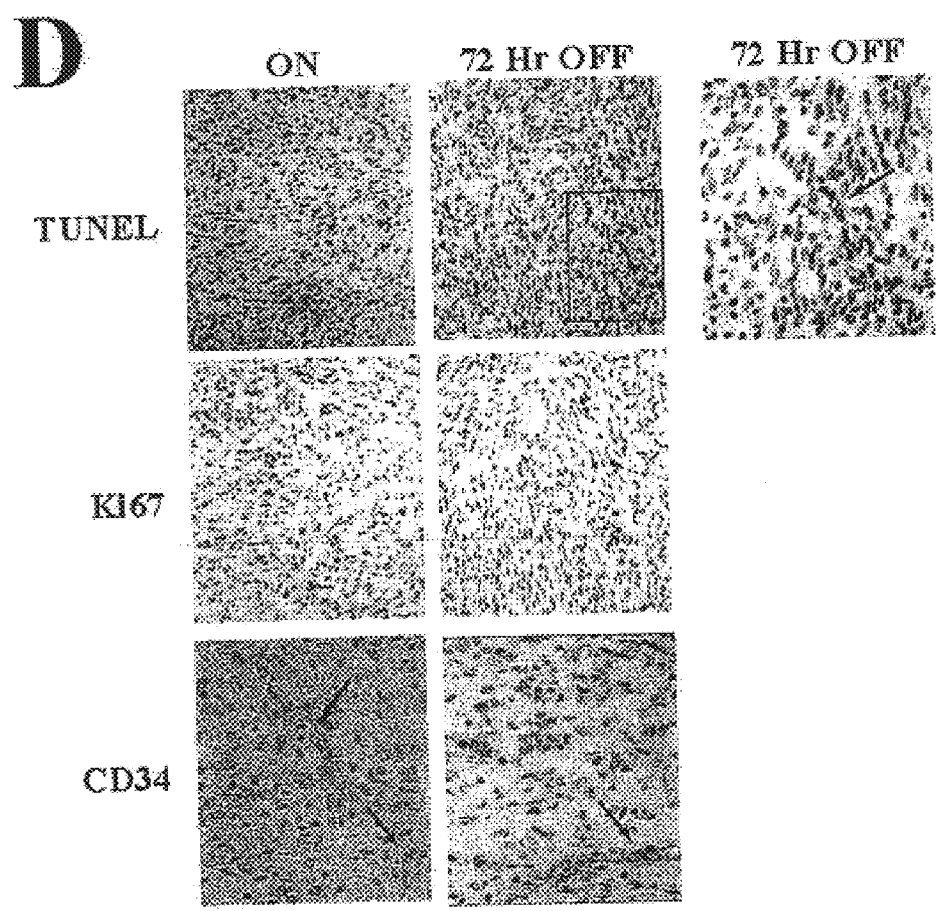

While these and previous results [5,7] confirm a causal role for H-RAS$^{V12G}$ in melanoma development, the capacity to regulate H-RAS$^{V12G}$ activity in these melanomas provided an unprecedented opportunity to. determine what role, if any, activated RAS plays in tumor maintenance. To this end, different doxycycline-treated Tyr/Tet-RAS INK4a−/− mice bearing one or multiple independent primary melanomas, ranging in size from 0.5 to 1.5 cm in diameter, were withdrawn from doxycycline administration (FIGS. 2A and 2B). Following an initial loss of tumor erythema (FIG. 2B, compare b to a), these large tumors regressed to barely detectable or undetectable masses with only residual scattered tumor foci on microscopic examination by day 14 of doxycycline withdrawal (FIG. 2C, compare right panel with left). Consistent with the presence of residual microscopic disease, re-administration of doxycycline resulted in the rapid recurrence of tumor at the site of the previous tumor (FIG. 2A). As such, this model may find use in the development of anti-oncologics directed towards minimal residual disease. All primary melanomas (n=10) exhibited regression upon doxycycline withdrawal; however, doxycycline-independent tumors can persist or re-emerge (n=3) particularly with large tumor burdens (See FIG. 2 legend). These latter tumors were whitish, exhibited a less anaplastic spindle cytology, failed to express the H-RAS$^{V12G}$ transgene by Western blot analyses, and were TRP-1 negative (data not shown). These data suggest that these doxycycline-independent tumors are either a different cancer type such as fibrosarcoma or RAS-independent melanomas.

Figure 3:
FIG. 3. In vitro and in vivo behavior of melanoma cells in the presence and absence of doxycycline.
Figure 3:
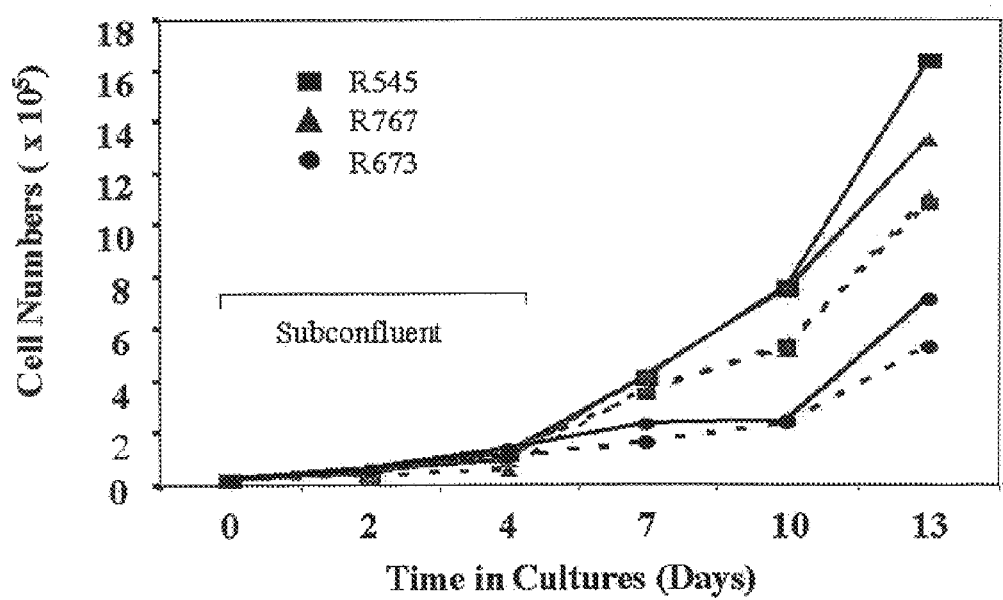

Although these results and those of others[8] underscore a role for RAS in tumorigenesis, this novel model system permits an investigation of mechanisms underlying tumor regression in vivo. To this end, we first assessed the impact of doxycycline withdrawal in different Tyr/Tet-RAS INK4a−/− tumor derived cell lines in cell culture. Melanoma cell lines were established from primary tumors in doxycycline-supplemented media and were shown to express H-RAS$^{V12G}$ mRNA, protein, and activity in a doxycycline-dependent manner (FIG. 4A and data not shown). The derivative melanoma cell lines remained doxycycline-responsive as shown by their strict doxycycline-dependency for tumorigenic potential in SCID mice. Specifically, subcutaneous injection of purified Tyr/Tet-RAS INK4a−/− melanoma cell lines yielded tumors in SCID mice treated with doxycycline with 100% efficiency, while those mice not receiving doxycycline remained tumor-free after many months of observation (FIG. 3A). In cell culture, the presence or absence of doxycycline did not significantly influence the subconfluent growth rates of multiple independently derived lines (FIG. 3B). Similarly, the presence of doxycycline failed to confer enhanced growth potential in low serum conditions (0.5% and 1% FCS) (data not shown). However, the presence of doxycycline modestly enhanced the growth in dense cultures, suggesting that in vivo RAS may provide a continued cell-autonomous advantage for tumor growth. On the other hand, the data is also consistent with the possibility that tumor regression following doxycycline withdrawal may reflect a continued requirement for RAS in promoting and sustaining non-cell-autonomous tumor-host interactions that are essential for tumor growth and maintenance.

One hypothesis supporting the latter possibility is that continued expression of RAS confers on the tumor cells the capacity to evade host immune response[9]; thus tumor regression occurs due to onset of immune rejection by the host. To examine the contribution of an intact immune system to tumor regression, we determined the regression kinetics of tumors derived from purified Tyr/Tet-RAS INK4a−/− melanoma cell lines in SCID tumor explants. Upon doxycycline withdrawal, established tumors exhibited rapid reductions in tumor size accompanied by histological, proliferative and apoptotic profiles that were indistinguishable from that of the primary tumors in immune competent hosts (data not shown). As SCID mice lack functioning B and T lymphocytes (though they maintain functional natural killer cells and macrophages), these data are consistent with the view that the immune system does not play a principal role during the initial phase in which the bulk of the tumor burden is eliminated.

Another important aspect of tumor reliance on host interactions involves angiogenic support. In fact, examination of regressing tumors suggested that vascular regression might even precede frank tumor loss. Serial biopsies of the same primary Tyr/Tet-RAS INK4a−/− tumors were performed following doxycycline withdrawal at times 0 hours, 24 hours, 48 hours and 72 hours. Tumor-bearing mice from both Tet-RAS founder lines #65 and #72 were examined (e.g. R348 and R405 from line #65 and #72, respectively) and yielded identical phenotypes. Upon microscopic examination, a morphologic transition from severe anaplasia to a more organized spindle cytoarchitecture occurred by 48 hours post doxycycline withdrawal (R348 tumor shown in FIG. 2C). A modest decline in proliferative index and a dramatic increase in apoptosis (R405 tumor shown in FIG. 2D) accompanied these histological changes. In many primary tumors examined, the apoptotic response was evident as early as 24 hours post doxycycline withdrawal (data not shown). Most notably, many TUNEL positive cells were found to reside in close proximity to small tumor vessels, specifically the cells comprising the vessel wall (FIG. 2D). Vessel-associated apoptosis coincided with a marked decrease in CD34 and CD31 immunoreactivity, two classical markers of the endothelial cell[10,11] (FIG. 2D, CD31 not shown).

The significant apoptotic rate of cells lining tumor vessels suggested that sustained activated RAS expression may be required for the critical host-tumor symbiotic interaction that sustains stable tumor vasculature. Consistent with this, previous cell culture data have shown that oncogenic K- and H-RAS$^{V12G}$ can stimulate VEGF gene expression[12-14]. To determine the role, if any, of VEGF in RAS-dependent tumor maintenance, RAS activity as measured by the RAF-GST pull-down assay and VEGF protein levels (see Methods) were serially determined in cell culture and tumor explants following doxycycline withdrawal. In cell culture, a decline in H-RAS$^{V12G}$ activity levels correlated with down-regulation of VEGF expression (FIG. 4A&B). In the tumor explants, although a decline in RAS activity led to an eventual decrease in VEGF levels during advanced stages of tumor regression (post day 3; FIGS. 4A and 4B), early regression and endothelial cell apoptosis occurred in the face of sustained VEGF levels, presumably due to hypoxic/anoxic stimuli[15-18]. The contrasting VEGF kinetics suggested that tumor regression in vivo is not mediated by the loss of RAS-stimulated VEGF expression and that high VEGF levels are insufficient to maintain tumor viability in the absence of H-RAS$^{V12G}$ expression. To examine this issue more directly, the doxycycline-responsive R545 melanoma cell line was engineered to constitutively express either GFP (green fluorescence protein) or VEGF plus GFP. The VEGF-transduced cell lines expressed on average 10-fold higher levels of VEGF than the GFP-transduced control in the absence of doxycycline (10 ng/ml versus<1 ng/ml by ELISA). Although the VEGF-transduced cells exhibited a more rapid tumor growth, doxycycline withdrawal resulted in regression of these tumors despite high level of enforced VEGF expression (FIG. 4C). Furthermore, as in primary tumors and SCID tumors derived from the parental untransduced melanoma lines, this tumor regression was associated with marked activation of apoptosis in both tumor cells and host endothelial cells (FIG. 4D).

Taken together, these data demonstrate that, while activated RAS regulates VEGF gene expression in tumor cells as previously reported[13,19-21], complex and poorly understood RAS-independent mechanisms contribute significantly to the regulation of VEGF in established tumors upon doxycycline withdrawal. Correspondingly, the fact that initiation of tumor regression and associated vascular collapse take place in the face of either robust endogenous or retrovirally-enforced VEGF expression indicates that VEGF is not sufficient for tumor maintenance, consistent with previous findings[14], and that the role of activated RAS in tumor maintenance extends beyond the regulation of VEGF gene expression. Thus, the in vivo model reported here will serve to uncover additional aspects of the complex homotypic and heterotypic interactions between host and tumor cells essential for the maintenance of fully formed solid tumors. While an improved understanding of such interactions could stimulate the development of therapeutics directed toward the less plastic host cell compartment, it is notable that despite the occurrence of many genetic changes in these tumors, effective anti-RAS therapeutics would be predicted to hold significant promise in an anti-cancer armamentarium.

Methods

Production of the transgenic mice. The reverse tetracycline transactivator (rtTA) is a 1050 bp EcoRI/BamHI fragment isolated from pUHD172-1neo[2]. The Tet promoter contains a XhoI/EcoRI fragment of CMV minimal promoter linked to the tet operator sequences[2]. The tyrosinase enhancer/promoter and the H-RAS$^{Val12}$ transgene were as described elsewhere[3,5,22]. Multiple founder lines were generated for both transgenes at the expected frequencies. One activator line (Tyr/rtTA, #37) and two independent reporter lines (Tet-RAS, #65 and #72) were utilized for these studies.

Primary tumors, derivative cell lines and SCID explant tumors. Transgenic mice were fed doxycycline drinking water (2 mg/ml sucrose water) and observed for spontaneous tumor development. Primary tumors were adapted to culture by mechanical mincing with sterilized razor blades and brief trypsinization and maintained on RPMI media containing 10% serum and supplemented with doxycycline (2 µg/ml media)[4]. For the SCID explant tumors, 2–5 1×10[6] established melanoma cells were injected SQ into the flanks of adult SCID mice maintained on doxycycline or regular drinking water. These cell lines were passaged sufficiently to insure elimination of immunocytes from the original host.

RNA and protein analysis. Total RNAs were isolated from tumor tissues and cells using Trizol reagents (Gibco BRL).

For H-RAS$^{V12G}$, a 700 bp SalI cDNA fragment isolated from pBABE-RAS (kind gift of Scott Lowe) was used as probe. For VEGF, a SacI/KpnI 600 bp ORF fragment was isolated from mVEGF.KS (kind gift of P. Maisonpierre). RNA in situ hybridization was performed as described elsewhere 23 on tumor samples snap-frozen in OCT (Lab-Tek). Western blots of tumor or cell lysates (100 μl input) were run on 15% SDS-PAGE gel and probed with Anti RAS MAB (Oncogene). RAS activity was determined by RAS Activation Assay (Upstate Biotechnology) as per manufacture's protocol. VEGF protein levels were determined in duplicate by ELISA (R&D System) using 100 mg of protein input (from tissue lysates or conditioned media). Microplates were ready by OPTIMax tunable microplate reader (Molecular Devices) and analyzed with SoftMax Pro.

Histological analyses and immunohistochemistry. Tissue samples were formalin fixed and paraffin embedded. Anti-TRP1 staining using TA99 monoclonal antibody[6], TUNEL, Ki67 and Anti-CD34 staining were performed as described elsewhere[5,11,24,25].

Growth curves. Cells from each cell line were seeded at a density of 20,000 cells per well in a 12-well plate in media with or without doxycycline. Media was changed every 3 days for all samples. Duplicate wells were trypsinized, cell numbers counted by hemacytometer at indicated time points and plotted against time. Studies were conducted in media containing 10%, 1% and 0.5% serum. Growth curve determinations were performed in cells maintained on doxycycline prior to experiments as well as cells already removed from doxycycline for 3 days.

Enforced VEGF expressing melanoma cell line. R545 melanoma cell line was transduced with LZRSpBMN-IRES-GFP and LZRSpBMN-VEGF-IRES-GFP purified populations established by FACS sorting[26]. SCID explant experiments with transduced cell lines were generated under the same conditions as described above. Tumor sizes were measured with tumor caliber in two dimensions and area plotted against time (in days).

Acknowledgments. The authors thank Dr. Gunther Schutz for the tyrosinase promoter-enhancer elements, Socorro Jiao for tissue sample processing and immunohistochemistry and Debra Compton for RNA in situ hybridization. AT is an HHMI Medical Student Fellow. LC is supported by NIH Mentored Clinician Scientist Award and the Harvard Skin Disease Center Grant. CCC and RAD are supported by grants from the NIH. RAD is an American Cancer Society Research Professor.

Bibliography

1. Bishop, J. M. Molecular themes in oncogenesis. Cell 64, 235–48: (1991).
2. Gossen, M., Freundlieb, S., Bender, G., Muller, G., Hillen, W. & Bujard, H. Transcriptional activation by tetracyclines in mammalian cells. Science 268, 1766–1769 (1995).
3. Fasano, O., Taparowsky, E., Fiddes, J., Wigler, M. & Goldfarb, M. Sequence and structure of the coding region of the human H-ras-1 gene from T24 bladder carcinoma cells. J. Mol. Appl. Genet. 2, 173–180 (1983).
4. Kistner, A., Gossen, M., Zimmermann, F., et al. Doxycycline-mediated quantitative and tissue-specific control of gene expression in transgenic mice. Proc. Natl. Acad. Sci. U.S.A. 93, 10933–10938 (1996).
5. Chin, L., Pomerantz, J., Polsky, D., et al. Cooperative effects of INK4a and ras in melanoma susceptibility in vivo. Genes Devel. 11, 2822–2834 (1997).
6. Thomson, T. M., Real, F. X., Murakami, S., Cordon-Cardo, C., Old, L. J. & Houghton, A. N. Differentiation antigens of melanocytes and melanoma: analysis of melanosome and cell surface markers of human pigmented cells with monoclonal antibodies. J. Invest. Dermatol. 90, 459–466 (1988).
7. Gause, P. R., Lluria-Prevatt, M., Keith, W. N., et al. Chromosomal and genetic alterations of 7,12-dimethylbenz[a]anthracene-induced melanoma from TP-ras transgenic mice. Mol. Carcin. 20, 78–87 (1997).
8. Shirasawa, S., Furuse, M., Yokoyama, N. & Sasazuki, T. Altered growth of human colon cancer cell lines disrupted at activated Ki-ras. Science 260, 85–88 (1993).
9. Doherty, P. C., Tripp, R. A. & Sixbey, J. W. Evasion of host immune responses by tumours and viruses. Ciba. Found. Symp. 187, 245–256 (1994).
10. Bird, I. N., Spragg, J. H., Ager, A. & Matthews, N. Studies of lymphocyte transendothelial migration: analysis of migrated cell phenotypes with regard to CD31 (PECAM-1), CD45RA and CD45RO. Immunology 80, 553–60: (1993).
11. Traweek, S. T., Kandalaft, P. L., Mehta, P. & Battifora, H. The human hematopoietic progenitor cell antigen (CD34) in vascular neoplasia. Am. J. Clin. Pathol. 96, 25–31: (1991).
12. Rak, J., Filmus, J., Finkenzeller, G., Grugel, S., Marme, D. & Kerbel, R. S. Oncogenes as inducers of tumor angiogenesis. Cancer & Metastasis Reviews 14, 263–277 (1995).
13. Arbiser, J. L., Moses, M. A., Fernandez, C. A., et al. Oncogenic H-ras stimulates tumor angiogenesis by two distinct pathways. Proc. Natl. Acad. Sci. USA 94, 861–866 (1997).
14. Okada, F., Rak, J. W., Croix, B. S., et al. impact of oncogenes in tumor angiogenesis: mutant K-ras up-regulation of vascular endothelial growth factor/vascular permeability factor is necessary, but not sufficient for tumorigenicity of human colorectal carcinoma cells. Proc. Natl. Acad. Sci. U.S.A. 95, 3609–14: (1998).
15. Shweiki, D., Itin, A., Soffer, D. & Keshet, E. Vascular endothelial growth factor induced by hypoxia may mediate hypoxia-initiated angiogenesis. Nature 359, 843–845 (1992).
16. Mazure, N. M., Chen, E. Y., Yeh, P., Laderoute, K. R. & Giaccia, A. J. Oncogenic transformation and hypoxia synergistically act to modulate vascular endothelial growth factor expression. Cancer Res. 56, 3436–3440 (1996).
17. Goldberg, M. A. & Schneider, T. J. Similarities between the oxygen-sensing mechanisms regulating the expression of vascular endothelial growth factor and erythropoietin. J. Biol. Chem. 269, 4355–4359 (1994).
18. Mukhopadhyay, D., Tsiokas, L., Zhou, X. M., Foster, D., Brugge, J. S. & Sukhatme, V. P. Hypoxic induction of human vascular endothelial growth factor expression through c-Src activation. Nature 375, 577–581 (1995).
19. Rak, J., Mitsuhashi, Y., Bayko, L., et al. Mutant ras oncogenes upregulate VEGF/VPF expression: implications for induction and inhibition of tumor angiogenesis. Cancer Res. 55, 4575–4580 (1995).
20. Grugel, S., Finkenzeller, G., Weindel, K., Barleon, B. & Marine, D. Both v-Ha-Ras and v-Raf stimulate expression of the vascular endothelial growth factor in NIH 3T3 cells. J. Biol. Chem. 270, 25915–25919 (1995).
21. Larcher, F., Robles, A. I., Duran, H., et al. Up-regulation of vascular endothelial growth factor/vascular permneability factor in mouse skin carcinogenesis correlates with malignant progression state and activated H-ras expression levels. Cancer Res 56, 5391–5396 (1996).
22. Ganss, R., Montoliu, L., Monaghan, A. P. & Schutz, G. A cell-specific enhancer far upstream of the mouse tyrosinase gene confers high level and copy number-related expression in transgenic mice. EMBO 13, 3083–3093 (1994).
23. Valenzuela, D. M., Stitt, T. N., DiStefano, P. S., et al. Receptor tyrosine kinase specific for the skeletal muscle lineage: expression in embryonic muscle, at the neuromuscular junction, and after injury. Neuron 15, 573–84: (1995).
24. Schreiber-Agus, N., Meng, Y., Hoang, T., et al. Role of Mxi1 in ageing organ systems and the regulation of normal and neoplastic growth. Nature 393, 483–7: (1998).
25. Gavrieli, Y., Sherman, Y. & Ben-Sasson, S. A. Identification of programmed cell death in situ via specific labeling of nuclear DNA fragmentation. J. Cell Biol. 119, 493–501: (1992).
26. Cheng, L., Fu, J., Tsukamoto, A. & Hawley, R. G. Use of green fluorescent protein variants to monitor gene transfer and expression in mammalian cells. Nat Biotechnol. 14, 606–609 (1996).

What is claimed:

1. A transgenic mouse, wherein the genome of said transgenic mouse comprises:
   (a) an expression construct comprising an oncogene operably linked to an inducible promoter, and
   (b) a genetic mutation that causes said transgenic mouse to have greater susceptibility to cancer than a mouse not comprising said genetic mutation,
      wherein expression of said oncogene is repeatedly inducible, reducible and re-inducible by controlling the activity of said inducible promoter;
      wherein induced expression of said oncogene leads to formation of cancer in said transgenic mouse; and
      wherein reduced expression of said oncogene as a result of reduced activity of said inducible promoter leads to regression of said cancer.

2. The transgenic mouse of claim 1, wherein said oncogene is ras.

3. The transgenic mouse of claim 2, wherein said ras has an activating mutation.

4. The transgenic mouse of claim 1, wherein said inducible promoter is inducible by doxycycline.

5. The transgenic mouse of claim 1, wherein said genetic mutation is in DNA encoding a tumor suppressor.

6. The transgenic mouse of claim 5, wherein said tumor suppressor is INK4.

7. The transgenic mouse of claim 5, wherein said tumor suppressor is INK4a.

8. A transgenic mouse, wherein the genome of said transgenic mouse comprises:
   (i) a first expression construct comprising a nucleic acid encoding a reverse tetracycline transactivator operably linked to a tissue-specific promoter;
   (ii) a second expression construct comprising an oncogene operably linked to a promoter that can be regulated by said reverse tetracycline transactivator and doxycycline; and
   (iii) a genetic mutation that causes said transgenic mouse to have greater susceptibility to cancer than a mouse not comprising said genetic mutation,
      wherein expression of said oncogene is repeatedly inducible, reducible and re-inducible by controlling the activity of said promoter that can be regulated by said reverse tetracycline transactivator and doxycycline;
      wherein expression of said reverse tetracycline transactivator in the presence of said doxycycline results in induced expression of said oncogene and leads to formation of cancer in said transgenic mouse, and
      wherein reduced expression of said oncogene as a result of reduced activity of said promoter that can be regulated by said reverse tetracycline transactivator and doxycycline leads to regression of said cancer.

9. The transgenic mouse of claim 8, wherein said tissue-specific promoter is a tyrosinase promoter.

10. A transgenic mouse, wherein the genome of said transgenic mouse comprises:
    (i) a first expression construct comprising a nucleic acid sequence encoding a reverse tetracycline transactivator operably linked to a tyrosinase promoter; and
    (ii) a second expression construct comprising a nucleic acid encoding ras operably linked to a promoter that can be regulated by said reverse tetracycline transactivator and doxycycline,
       wherein expression of ras is repeatedly inducible, reducible and re-inducible by controlling the activity of said promoter that can be regulated by said reverse tetracycline transactivator and doxycycline;
       wherein expression of said reverse tetracycline transactivator in the presence of said doxycycline results in induced expression of said ras and formation of cancer in said transgenic mouse, and
       wherein reduced expression of said oncogene as a result of reduced activity of said promoter that can be regulated by said reverse tetracycline transactivator and doxycycline leads to regression of said cancer.

11. The transgenic mouse of claim 10, wherein the genome of said transgenic mouse further comprises a genetic mutation that causes said transgenic mouse to have greater susceptibility to cancer than a mouse not comprising said genetic mutation.

12. A method for making a transgenic mouse model for cancer maintenance, said method comprising:
    (a) obtaining a first mouse comprising an expression construct comprising an oncogene operably linked to an inducible promoter;
    (b) obtaining a second mouse comprising a genetic mutation that causes said second mouse to have greater susceptibility to cancer than a mouse not comprising said genetic mutation; and
    (c) crossing said first mouse with said second mouse to obtain a transgenic mouse comprising said expression construct and said genetic mutation,
       wherein expression of said oncogene is repeatedly inducible, reducible and re-inducible by controlling the activity of said inducible promoter;
       wherein induced expression of said oncogene leads to formation of cancer in said transgenic mouse, and
       wherein reduced expression of said oncogene as a result of reduced activity of said inducible promoter leads to regression of said cancer, said transgenic mouse being said transgenic mouse model.

13. The method of claim 12, wherein said oncogene is ras.

14. The method of claim 13, wherein said ras has an activating mutation.

15. The method of claim 12, wherein said inducible promoter is inducible by doxycycline.

16. The method of claim 12, wherein said genetic mutation is in DNA encoding a tumor suppressor.

17. The method of claim 16, wherein said tumor suppressor is INK4a.

18. A mouse tumor cell in vitro, wherein said mouse tumor cell was derived from a transgenic mouse, wherein the genome of said transgenic mouse comprises:
  (a) an expression construct comprising an oncogene operably linked to an inducible promoter, wherein expression of said oncogene is repeatedly inducible, reducible and re-inducible; and
  (b) a genetic mutation that causes said transgenic mouse to have greater susceptibility to cancer than a mouse not comprising said genetic mutation,
    wherein said mouse tumor cell comprises said expression construct and said genetic mutation, and wherein maintenance of said mouse tumor cell in a SCID mouse requires expression of said oncogene.

19. The mouse tumor cell of claim 18, wherein said oncogene is ras.

20. The mouse tumor cell of claim 19, wherein said ras has an activating mutation.

21. The mouse tumor cell of claim 18, wherein said inducible promoter is inducible by doxycycline.

22. The mouse tumor cell of claim 18, wherein said genetic mutation is in a tumor suppressor gene.

23. The mouse tumor cell of claim 22, wherein said tumor suppressor gene is INK4a.

24. A tumor cell, wherein the genome of said tumor cell comprises:
  (a) an expression construct comprising an oncogene operably linked to an inducible promoter, wherein expression of said oncogene is repeatedly inducible, reducible and re-inducible; and
  (b) a genetic mutation in a tumor suppressor gene,
    wherein maintenance of said tumor cell in a SCID mouse requires expression of said oncogene.

25. The tumor cell of claim 24, wherein said oncogene is ras.

26. The tumor cell of claim 25, wherein said ras has an activating mutation.

27. The tumor cell of claim 24, wherein said inducible promoter is inducible by doxycycline.

28. The tumor cell of claim 24, wherein said tumor suppressor gene is INK4a.

29. The tumor cell of claim 24, wherein said tumor cell was derived from a transgenic mouse, the genome of said transgenic mouse comprising said expression construct.

30. A tumor explant from a transgenic mouse, wherein the genome of said transgenic mouse comprises:
  (a) an expression construct comprising an oncogene operably linked to an inducible promoter, wherein expression of said oncogene is repeatedly inducible, reducible and re-inducible; and
  (b) a genetic mutation that causes said transgenic mouse to have greater susceptibility to cancer than a mouse not comprising said genetic mutation,
    wherein maintenance of said tumor explant in a SCID mouse requires expression of said oncogene.

31. The tumor explant of claim 30, wherein said oncogene is ras.

32. The tumor explant of claim 31, wherein said ras has an activating mutation.

33. The tumor explant of claim 30, wherein said inducible promoter is inducible by doxycycline.

34. The tumor explant of claim 30, wherein said genetic mutation is in a tumor suppressor gene.

35. The tumor explant of claim 34, wherein said tumor suppressor gene is INK4a.

36. A method for determining whether an oncogene contributes to tumor maintenance, said method comprising:
  (a) providing a transgenic mouse, wherein the genome of said transgenic mouse comprises:
    (i) an expression construct comprising said oncogene operably linked to an inducible promoter, wherein expression of said oncogene is repeatedly inducible, reducible and re-inducible; and
    (ii) a genetic mutation that causes said transgenic mouse to have greater susceptibility to cancer than a mouse not comprising said genetic mutation,
      wherein said transgenic mouse comprises a tumor formed in said transgenic mouse during expression of said oncogene; and
  (b) determining whether or not said tumor regresses when expression of said oncogene is reduced, wherein tumor regression indicates that said oncogene contributes to tumor maintenance.

37. The method of claim 36, wherein said oncogene is ras.

38. The method of claim 37, wherein said ras has an activating mutation.

39. The method of claim 36, wherein said inducible promoter is inducible by doxycycline.

40. The method of claim 36, wherein said genetic mutation is in DNA encoding a tumor suppressor.

41. The method of claim 37, wherein said tumor suppressor is INK4a.

42. A method for determining whether a transgenic mouse has minimal residual disease, wherein the genome of said transgenic mouse comprises:
  (a) an expression construct comprising an oncogene operably linked to an inducible promoter, wherein expression of said oncogene is repeatedly inducible, reducible and re-inducible; and
  (b) a genetic mutation that causes said transgenic mouse to have greater susceptibility to cancer than a mouse not comprising said genetic mutation;
    said method comprising determining whether or not tumor recurrence occurs at a site of a previous tumor during expression of said oncogene, wherein said previous tumor was formed during expression of said oncogene and regressed when expression of said oncogene was reduced, wherein tumor recurrence at said site indicates that said transgenic mouse has said minimal residual disease.

43. The method of claim 42, wherein said oncogene is ras.

44. The method of claim 43, wherein said ras has an activating mutation.

45. The method of claim 42, wherein said inducible promoter is inducible by doxycycline.

46. The method of claim 42, wherein said genetic mutation is in DNA encoding a tumor suppressor.

47. The method of claim 46, wherein said tumor suppressor is INK4a.

* * * * *